United States Patent [19]

Ritter, II

[11] Patent Number: 4,512,913
[45] Date of Patent: Apr. 23, 1985

[54] SOL-GEL SOLUTION PREPARATION

[75] Inventor: George W. Ritter, II, Newark, Ohio

[73] Assignee: Owens-Corning Fiberglas Corporation, Toledo, Ohio

[21] Appl. No.: 397,667

[22] Filed: Jul. 12, 1982

[51] Int. Cl.$^3$ .................... B01J 13/00; C09K 3/00
[52] U.S. Cl. .................... 252/313.1; 106/287.17; 252/315.7
[58] Field of Search ............... 252/313 R, 315.7, 309; 106/287.17, 38.35; 424/47

[56] References Cited

U.S. PATENT DOCUMENTS

| | | | |
|---|---|---|---|
| 2,607,658 | 8/1952 | Govett | 252/317 |
| 2,773,839 | 12/1956 | Stover | 252/315.7 X |
| 2,900,349 | 8/1959 | Schwartz | 252/317 |
| 2,955,915 | 10/1960 | Bicek | 252/315.7 |
| 3,105,053 | 9/1963 | Cramer | 252/313 |
| 3,555,146 | 1/1971 | Jones | 424/47 |
| 3,761,500 | 9/1973 | Thomas . | |
| 3,786,137 | 1/1974 | Thomas . | |
| 3,855,147 | 12/1974 | Granguist | 106/287.17 X |
| 3,876,758 | 4/1975 | Beekman | 424/47 |
| 3,895,956 | 7/1975 | Yoshida | 106/287.17 X |
| 3,966,996 | 6/1976 | Andre | 423/626 |
| 4,017,599 | 4/1977 | Rubino | 424/47 |
| 4,089,692 | 5/1978 | Toeniskoetter | 106/38.35 |
| 4,196,011 | 4/1980 | Koike | 106/38.2 |
| 4,211,667 | 7/1980 | Yamada | 252/313 R |
| 4,333,846 | 6/1982 | Lee | 252/184 |
| 4,342,664 | 8/1982 | Blome | 252/313 R |
| 4,354,872 | 10/1982 | Kekish | 252/309 X |

FOREIGN PATENT DOCUMENTS

| | | | |
|---|---|---|---|
| 138960 | 2/1948 | Australia | 106/38.35 |
| 542257 | 6/1957 | Canada | 252/315.7 |
| 594671 | 11/1947 | United Kingdom | 106/38.35 |

*Primary Examiner*—Richard D. Lovering
*Assistant Examiner*—Catherine S. Kilby
*Attorney, Agent, or Firm*—Ronald C. Hudgens; Robert F. Rywalski

[57] ABSTRACT

A method of producing a hydrosol which comprises reacting a Group II water-soluble metal salt with an aluminum chlorohydrate-organic complex to produce a hydrosol and incorporating into said hydrosol a viscosity inhibitor selected from the group consisting of water soluble ether alcohols, ethers, alcohols and mono-protic acid salts of triethanol amine.

10 Claims, No Drawings

SOL-GEL SOLUTION PREPARATION

TECHNICAL FIELD

This invention pertains to the production of sol-gel solutions.

In one of its more specific aspects, this invention pertains to the preparation of magnesium-containing complexes suitable for use in the production of films, molded products and fibers. The formation of gels containing such materials as alumina, silica, lithium, titanium, manganese and magnesium for the production of fibers is well known. The name "National Felt" which appears on the specimens refers to applicant's wholly owned manufacturing subsidiary corporation.

STATEMENT OF THE INVENTION

There has now been developed a method of producing a hydrosol, a water-based gel, which is simple, rapid and which gel has been found to produce films, molded products and fibers. This method comprises reacting a Group II water-soluble metal salt with an aluminum chlorohydrate-organic complex and removing water from the resulting mixture to form a gel. To the gel is then added a viscosity control agent to produce the final product.

DESCRIPTION OF THE INVENTION

The method of this invention is generally applicable to the use of any Group II water-soluble metal salt, or mixtures thereof. In its preferred embodiment, it is particularly applicable to the use of anhydrous magnesium chloride and, preferably, to the use of magnesium chloride hexahydrate.

The aluminum chlorohydrate-organic complex will preferably be employed in the form of an aluminum chlorohydroxide-propylene glycol complex having an aluminum oxide content equivalent to approximately 36 weight percent, about 12.5 weight percent chloride, about 25 weight percent propylene glycol, with an Al:Cl atomic ratio in the range of from about 2:1 to about 1.9:1.

One particularly suitable aluminum chlorohydrate-glycol complex is commercially available as Rehydrol II from Reheis Chemical Company, Berkeley Heights, N.J. However, any suitable aluminum chlorohydrate-organic complex can be employed as, for example, one containing propylene or ethylene glycol.

In general, the method of this invention is carried out by mixing an aqueous solution of the Group II metal chloride and a solution of aluminum chlorohydrate-organic complex. These two materials can be reacted in a ratio of from about 5 to about 50 parts of the Group II metal chloride to about 95 to about 50 parts of the aluminum chlorohydrate-organic complex.

To the resultant solution is preferably added concentrated hydrochloric acid which serves to stabilize the gel and prevent macro-precipitation. If added, the hydrochloric acid is added in an amount of at least about 1.25 weight percent per part by weight of the resultant solution.

The resulting solution is distilled under reduced pressure to remove a portion of the water and to produce a product containing about 52 weight percent solids. The resulting material is recovered and aged to produce a gel.

Any suitable viscosity control agent can be employed. Preferably, the agent will be a water soluble material selected from the group consisting of ether alcohols, ethers, alcohols and mono-protic acid salts of triethanolamine. In general, the agent will contain from about three to about six oxygen atoms per molecule. These agents are added to the gel in an amount within the range of from about 1.5 weight percent to about 4 weight percent of the hydrosol and, preferably, in an amount of about 2 weight percent.

Suitable agents include ethyleneglycoldiacetate, 2-(2-methoxyethoxy)ethanol and triethanolammonium hydrochloride.

The following examples demonstrate the preparation of the water-based gel concerned in this invention.

EXAMPLE I 571 g. $MgCl_2.6H_2O$ were dissolved in 850 g. distilled water. To the resulting solution were added 34 ml. concentrated HCl. 850 g. of Rehydrol II were added in small portions over a period of five minutes. Thereafter the mixture was agitated for five minutes.

The mixture was then distilled under reduced pressure to remove 120 g. of water and to yield 2,140 g. of solution containing about 52 weight percent solids. The gel was refluxed at atmospheric pressure for 21 hours. The solution was aged at 40° C. for six days to give a viscous, transparent material having a viscosity of about 380 poise at 39° C., and a specific gravity of about 1.35. The material was then stored at room temperature for seven days.

The following example illustrates the use of the agents of this invention.

EXAMPLE II

To four 100 g. portions of the gel prepared in Example I were added the agents set forth below. No inhibitor was added to the fifth portion.

| Portion | Viscosity Agent | Amount, g. |
|---|---|---|
| 1 | Ethyleneglycoldiacetate | 3.7 |
| 2 | 2-(2-Methoxyethoxy)Ethanol | 1.6 |
| 3 | Triethanolammonium Chloride | 2.4 |
| 4 | 2-Methoxyethyl Ether | 1.9 |
| 5 | None | 0 |

All mixtures were homogenized at 60° C. for one hour. However, Portion 1 showed immiscibility after 24 hours at 40° C.

Viscosity measurements after various intervals thereafter were as follows, interim storage being at 40° C.

| Portion | Viscosity, poise | Temperature, °C. |
|---|---|---|
| I. After 48 Total Hours | | |
| 2 | 25.4 | 59.2 |
| 3 | 20.0 | 59.7 |
| 4 | 19.5 | 59.7 |
| 5 | 86.0 | 60.0 |
| II. After 96 Total Hours | | |
| 4 | 10.9 | 60.2 |
| 4 | 13.3 | 58.7 |
| 5 | 228 | 59.6 |
| III. After 168 Total Hours | | |
| 4 | 44.5 | 59.1 |

These data indicate the effect of the agents involved in acting to limit viscosity increase.

It will be evident from the foregoing that various methods can be made to the method of this invention.

Such, however, are considered within the scope of this invention.

I claim:

1. A method of producing a hydrosol which comprises reacting a Group II water soluble metal salt with an aluminum chlorohydrate-alkylene glycol complex to produce a hydrosol and incorporating into said hydrosol a viscosity control agent selected from the group consisting of water soluble ether alcohols, ethers, and monoprotic acid salts of triethanol amine.

2. The method of claim 1 wherein said viscosity control agent contains from about 3 to about 6 oxygen atoms per molecule.

3. The method of claim 1 wherein said viscosity control agent is selected from the group consisting of ethyleneglycoldiacetate, 2-methoxyethyl ether, and triethanolammonium hydrochloride.

4. The method of claim 1 in which said viscosity control agent is incorporated into said hydrosol in an amount within the range of from about 1.5 to about 4 weight percent of the hydrosol.

5. The method of claim 1 in which said viscosity control agent is incorporated into said hydrosol in an amount of about 2 weight percent of the hydrosol.

6. A hydrosol comprising the reaction product of a Group II water-soluble metal salt with an aluminum chlorohydrate-alkylene glycol complex and a material selected from the group consisting of water soluble ether alcohols, ethers, and mono-protic acid salts of triethanolamine.

7. The hydrosol of claim 6 in which said material contains from about 3 to about 6 oxygen atoms per molecule.

8. The hydrosol of claim 6 in which said material is selected from the group consisting of:
ethyleneglycoldiacetate,
triethanolammonium hydrochloride, and
2-methoxyethyl ether.

9. The hydrosol of claim 6 in which said material is incorporated in said reaction product in an amount within the range of from about 1.5 weight percent to about 4 weight percent.

10. The hydrosol of claim 8 in which said material is 2-methoxyethyl ether and is incorporated in said hydrosol in an amount of about 1.9 parts by weight per 100 parts of said hydrosol.

* * * * *